(12) United States Patent
Elyasaf et al.

(10) Patent No.: US 7,355,690 B2
(45) Date of Patent: Apr. 8, 2008

(54) DOUBLE INSPECTION OF RETICLE OR WAFER

(75) Inventors: Emanuel Elyasaf, Rehovot (IL); Oren Boiman, Tel-Aviv (IL)

(73) Assignee: Applied Materials, Israel, Ltd., Rehovot (IL)

( * ) Notice: Subject to any disclaimer, the term of this patent is extended or adjusted under 35 U.S.C. 154(b) by 435 days.

(21) Appl. No.: 10/780,374

(22) Filed: Feb. 17, 2004

(65) Prior Publication Data

US 2005/0018899 A1    Jan. 27, 2005

Related U.S. Application Data

(60) Provisional application No. 60/489,057, filed on Jul. 21, 2003.

(51) Int. Cl.
    *G01N 21/00*   (2006.01)

(52) U.S. Cl. .................................. 356/237.2; 356/237.5
(58) Field of Classification Search ............. 356/237.1, 356/237.2, 237.5
    See application file for complete search history.

(56) References Cited

U.S. PATENT DOCUMENTS

2003/0058435 A1* 3/2003 Honda et al. ............ 356/237.1

* cited by examiner

*Primary Examiner*—Roy M Punnoose
(74) *Attorney, Agent, or Firm*—Tarek N. Fahmi

(57) ABSTRACT

During mask or reticle inspection, each region is scanned at least twice, using an overlap between each pair of consecutive frames. System contamination and camera blemishes have approximately constant frame coordinates, while mask defects have constant reticle coordinates, but inconstant scan frame coordinates. True defects are detected at different coordinates in consecutive frames with a known displacement therebetween.

23 Claims, 7 Drawing Sheets

DOUBLE INSPECTION OF RETICLE OR WAFER

CROSS-REFERENCE TO RELATED APPLICATIONS

This application claims the benefit of Provisional Application No. 60/489,057 titled "Double inspection on reticle/wafer, filed 21 Jul. 2003.

BACKGROUND OF THE INVENTION

1. Field of the Invention

This invention relates to inspection of articles related to the manufacture of semiconductor devices. More particularly, this invention relates to the inspection of photomasks or reticles used in the photolithographic manufacture of semiconductor devices.

2. Description of the Related Art

Modern microelectronic devices are commonly produced using a photolithographic process. In this process, a semiconductor wafer is first coated with a layer of photoresist. In one important technique of production, masks or reticles are used to transfer circuitry patterns to semiconductor wafers. Although there are differences in usage of the terms "mask" and "reticle," for the purposes of the present invention the terms are interchangeable, and references hereinbelow to either of these terms should be understood as including both masks and reticles, unless otherwise specified. Typically, the reticles are in the form of patterned chrome over a transparent substrate. A series of such reticles are employed to project the patterns onto the wafer in a preset sequence. Each photolithographic reticle includes an intricate set of geometric patterns corresponding to the circuit components to be integrated onto the wafer. The transfer of the reticle pattern onto the photoresist layer is performed by an optical exposure tool such as a scanner or a stepper, which directs light or other radiation through the reticle to expose the photoresist. The photoresist is thereafter developed to form a photoresist mask, and underlying polysilicon insulation or a metal layer is selectively etched in accordance with the mask to form features such as lines or gates.

It should be appreciated by those skilled in the art that to produce an operational microelectronic circuit, a mask must be as defect-free as possible, preferably completely defect-free. Therefore, mask inspection tools are needed to detect various defects in the masks that can potentially reduce the microelectronic circuit fabrication yields. Smaller feature sizes of the masks used in the microphotolithographic process, as well as the use of phase shift and OPC masks, require more sophisticated tools for mask inspection. For instance, the inspection of phase shift masks requires not only finding "conventional" defects, such as particles, but also detecting errors in the thickness of various regions of the mask. Numerous systems for mask inspection have been developed in response to the growing demands of the electronic industry.

From the above description, it should be appreciated that any defect on the reticle, such as extra or missing chrome, may transfer onto the fabricated wafer in a repeated manner. Thus, any defect on the reticle would drastically reduce the yield of the fabrication line. Therefore, it is important to inspect the reticles carefully, and detect any defects thereupon. The inspection is generally performed by an optical system, using transmitted, reflected, or both types of illuminations. An example of such a system is the ARIS21i reticle inspection system available from Applied Materials, Inc., 2821 Scott Boulevard, Santa Clara, Calif. 95050.

There are several known algorithmic methods for inspection of reticles. These methods include: die-to-die inspection, in which a die is compared to a purportedly identical die on the same reticle; and "die-to-database" inspection, in which data pertaining to a given die is compared to information in a database, which could be the one from which the reticle was generated. In another inspection method, die-to-golden-die, a reference die is chosen for inspecting wafers. There also is a design rule based inspection, in which the die has to fulfill line width and spacing requirements, and feature shapes should fit predefined shapes. Examples of these inspection methods, and relevant apparatus and circuitry for implementing these methods, are described in various U.S. patents, including, inter alia, U.S. Pat. Nos. 4,805,123, 4,926,489, 5,619,429, and 5,864,394. The disclosures of these patents are incorporated herein by reference. A die-to-database inspection system is available as the model ARIS100i from Applied Materials, Inc.

Known inspection techniques typically image the article under inspection using a large magnification onto a solid state imaging device, such as a charge-coupled device (CCD) camera. The imaging technique requires the article to be illuminated. The brightness of the illuminating source is a key factor in the ability to speed the inspection by reducing the integration time of the camera. As the patterns on wafers become smaller, it becomes necessary to use smaller wavelengths in order to be able to detect the patterns. This is due to the fact that the physical resolution limit depends linearly on the illumination wavelength, and further due to interference effects, which require that the inspection be done at a wavelength similar to the one used in the lithographic process. As the wavelengths become smaller, conventional incoherent light sources like filament lamps or gas discharge lamps do not have enough brightness, and the light sources of choice become short wavelength lasers. The coherence of the laser, roughness and aberrations of the optical surfaces used in the inspection system, and patterns on the article (such as circuit patterns on a mask, reticle or semiconductor wafer) along the light path combine to create artifacts due to interference and diffraction of the laser beam.

Inspection systems used to detect manufacturing defects can be classified by two interdependent factors: detection rate and false alarm rate (FA rate), referred to herein as false positive detection. Optical inspection systems using CCD/CMOS cameras can suffer from contamination or scratches on the optical surfaces and from detector problems (blemishes, dead pixels, etc.) Such defects can cause artifact images at the CCD plane of the inspection system, especially under high coherence illumination, which may hide actual defects on the article under inspection. The artifacts dynamically change, depending on the article pattern, since the pattern on the article influences the diffraction pattern generated at the CCD plane by a contaminant particle or scratch. The article patterns thus affect the FA rate, an effect that can not be neutralized by calibration procedures. For efficient inspection, there is a need to maintain a low FA rate, while still providing high inspection throughput.

SUMMARY OF THE INVENTION

Aspects of the present invention are directed to alleviating the problem of false positive detection caused by system artifacts. According to a disclosed embodiment of the invention, each region on an article under inspection, such as a mask, is scanned, or otherwise illuminated, at least twice during inspection, using an overlap between each two consecutive frames in the scanning direction. Typically consecutive frames overlap by at least 50 percent. However in some applications, it is possible to reduce the overlap below 50 percent In different scans, system blemishes have approximately constant frame coordinates, while mask defects have constant reticle coordinates, but inconstant scan frame coordinates. These facts enable distinction between real defects and system artifacts that imitate defects. True defects are detected at different coordinates in consecutive frames with a known frame displacement therebetween, while system artifacts are not displaced on different frames.

The overlapping frame images may be captured by scanning a single camera over the article at reduced speed. In some embodiments, however, in order to maintain high throughput, multiple cameras with adjacent or overlapping fields of view scan over the article together, in parallel. As different cameras generally have blemishes in different frame locations, the output of one camera can be used to detect defects positioned at a blemish location of another.

In an alternate disclosed embodiment of the invention, multiple cameras image the same field of view simultaneously, but at different defocus. Imaging optics comprising a system of mirrors and beamsplitters are positioned so as to direct a portion of the light returning from the field of view onto a respective camera. The cameras may be positioned, for example, so that each camera is at a different optical distance from the article and thus images the article at a different defocus. This mode is useful, inter alia, in process window inspection, for checking printability of a mask over a given defocus range.

In an alternate embodiment of the invention beam directing optics are operative in a first mode in which overlapping images are acquired, or in a second, fast scan mode, in which each camera images its own field of view in the article plane without overlapping.

In an alternate embodiment of the invention, multiple passes across a mask are made in which there is an overlap between slices that are orthogonal to the scan direction.

The invention provides a method of inspecting an article, which is carried out by acquiring a first frame image of a first field of view of the article, and acquiring a second frame image of a second field of view of the article, wherein the first field of view and the second field of view overlap, and identifying blemish locations having substantially constant frame coordinates on the first frame image and the second frame image.

An aspect of the method includes identifying a first defect location on the first frame image and a second defect location on the second frame image. The first defect location is displaced from the second defect location by a frame displacement that is defined by the overlap, wherein at least one of the first defect location and the second defect location is distinct from any of the blemish locations.

According to another aspect of the method, both of the first defect location and the second defect location are distinct from the blemish locations.

A further aspect of the method includes adjusting the overlap such that the frame displacement is distinct from displacements between pairs of system blemishes that are aligned in a scan direction.

One aspect of the method includes varying a detection threshold of the first frame image and the second frame image, and repeatedly identifying a first defect location on the first frame image and a second defect location on the second frame image, so as to identify all defect locations on the article.

Still another aspect of the method includes applying a super-resolution technique to the first frame image and the second frame image, and repeating the identification of the first defect location on the first frame image and the second defect location on the second frame image, so as to identify all defect locations on the article.

In still another aspect of the method the first frame image the second frame image are acquired by impinging pulsed coherent light on the article.

According to another aspect of the method, the focal plane of the first frame image differs from the focal plane of the second frame image.

According to yet another aspect of the method, the overlap of the first field of view and the second field of view is oriented in the scan direction.

According to still another aspect of the method, the overlap of the first field of view and the second field of view is oriented orthogonal to the scan direction.

According to yet another aspect of the method, the overlap is at least 50% of an area of the first frame image.

The invention provides a method of inspecting an article employing an optical imaging system, which is carried out by preparing a pre-scan mask of blemishes of the optical imaging system, determining blemish displacements between pairs of the blemishes that are aligned in the scan direction, selecting a frame overlap of consecutive image frames of the article that is distinct from all of the blemish displacements, acquiring a first frame image and acquiring a second frame image of the article that overlaps the first frame image at the frame overlap, and masking the first frame image and the second frame image with the pre-scan mask.

An additional aspect of the method includes identifying a first defect location on the first frame image and a second defect location on the second frame image, wherein the first defect location is displaced from the second defect location by a frame displacement that is defined by the frame overlap between the first frame image and the second frame image, wherein at least one of the first defect location and the second defect location is distinct from any of the blemishes on the pre-scan mask.

An additional aspect of the method includes varying a detection threshold of the first frame image and the second frame image, and repeating the procedure for identifying the first defect location on the first frame image and the second defect location on the second frame image, so as to identify all defect locations on the article.

The invention provides an optical inspection apparatus of inspecting an article, including a scanner for illuminating the article in a scan direction, a detector for detecting frame images of the article, beam directing optics for directing light from the article to the detector, a controller for controlling the scanner and the detector to acquire the frame images portions at a frame overlap, and an image processor adapted to prepare a pre-scan mask of system blemishes. The frame overlap is selected to be distinct from all displacements between pairs of the blemishes that are aligned in the scan direction. The image processor is further adapted to mask the frame images with the pre-scan mask.

According to another aspect of the optical inspection apparatus, the detector includes a plurality of cameras that simultaneously image overlapping fields of view on the article.

According to a further aspect of the optical inspection apparatus, the detector includes a plurality of cameras, and the controller in a first mode of operation configures the cameras to image overlapping fields of view on the article and in a second mode of operation configures the cameras to image adjacent non-overlapping fields of view thereon.

The invention provides a method of inspecting an article, which is carried out by directing a beam from the article through optics along a plurality of optical paths, disposing a first camera in one of the optical paths, the first camera having a first field of view of the article and disposing a second camera in another of the optical paths, the second camera having a second field of view of the article, wherein the first field of view and the second field of view have an overlap. The method is further carried out by acquiring a first frame image of the article with the first camera, and acquiring a second frame image of the article with the second camera, identifying blemish locations having substantially constant frame coordinates on the first frame image and the second frame image, and identifying a defect in the first frame image and in the second frame image, wherein the frame displacement of the defect corresponds to the overlap, and wherein a location of the defect on at least one of the first frame image and the second frame image avoids the frame coordinates of the blemish locations thereon.

According to yet another aspect of the method, frame coordinates of the defect on the first frame image and on the second frame image are distinct from the blemish locations.

A further aspect of the method includes adjusting the overlap such that the frame displacement is unequal to any displacement between members of pairs of system blemishes that are aligned in a scan direction.

The invention provides an optical inspection apparatus, including a plurality of image sensors, and beam directing optics, which are adapted to direct a collection beam from a surface of an article under inspection onto the image sensors. In a first configuration the optics direct the collection beam onto the image sensors, so that all the image sensors have a common field of view, and in a second configuration the image sensors have different fields of view.

According to an aspect of the optical inspection apparatus, the optics impinge the collection beam onto the image sensors with equal fluence.

According to another aspect of the optical inspection apparatus, the image sensors comprise three detectors, and the optics comprise two mirrors.

According to still another aspect of the optical inspection apparatus, in the first configuration the image sensors are focused on different planes relative to a surface of the article.

According to yet another aspect of the optical inspection apparatus, in the second configuration the first field of view overlaps the second field of view.

Still another aspect of the optical inspection apparatus includes at least one beam splitter disposed in the collection beam for directing at least portions of the collection beam toward the image sensors, respectively.

According to a further aspect of the optical inspection apparatus, the beam splitter includes two beam splitters, and the image sensors comprise three image sensors.

One aspect of the optical inspection apparatus includes a mirror disposed in the collection beam, and a beam blocking means moveable to block a portion of the collection beam from reaching the mirror, and an opto-mechanical subsystem for displacing the beam blocking means and the beam splitter between operating positions and non-operating positions, and a scanner, wherein the article is scanned relative the optics in a scan direction. In the first configuration the beam blocking means is interposed by the opto-mechanical subsystem so as to block the portion of the collection beam, and the beam splitter is disposed within the collection beam, and in the second configuration the beam blocking means and the beam splitter are displaced by the opto-mechanical subsystem external to the collection beam. The first field of view and the second field of view overlap, and the frame displacement between the first field of view and the second field of view is distinct from displacements between members of pairs of system blemishes that are aligned in the scan direction.

The invention provides a method of inspecting an article, which is carried out by disposing a plurality of image sensors to image the article, and directing a collection beam from a surface of the article under inspection onto the image sensors. In a first configuration, all the image sensors have a common field of view, and in a second configuration, the image sensors have different fields of view.

BRIEF DESCRIPTION OF THE DRAWINGS

For a better understanding of the present invention, reference is made to the detailed description of the invention, by way of example, which is to be read in conjunction with the following drawings, wherein like elements are given like reference numerals, and wherein.

DETAILED DESCRIPTION OF THE INVENTION

In the following description, numerous specific details are set forth in order to provide a thorough understanding of the present invention. It will be apparent to one skilled in the art, however, that the present invention may be practiced without these specific details. In other instances well-known circuits, control logic, and the details of computer program instructions for conventional algorithms and processes have not been shown in detail in order not to unnecessarily obscure the present invention.

Embodiment 1

Figure 1:
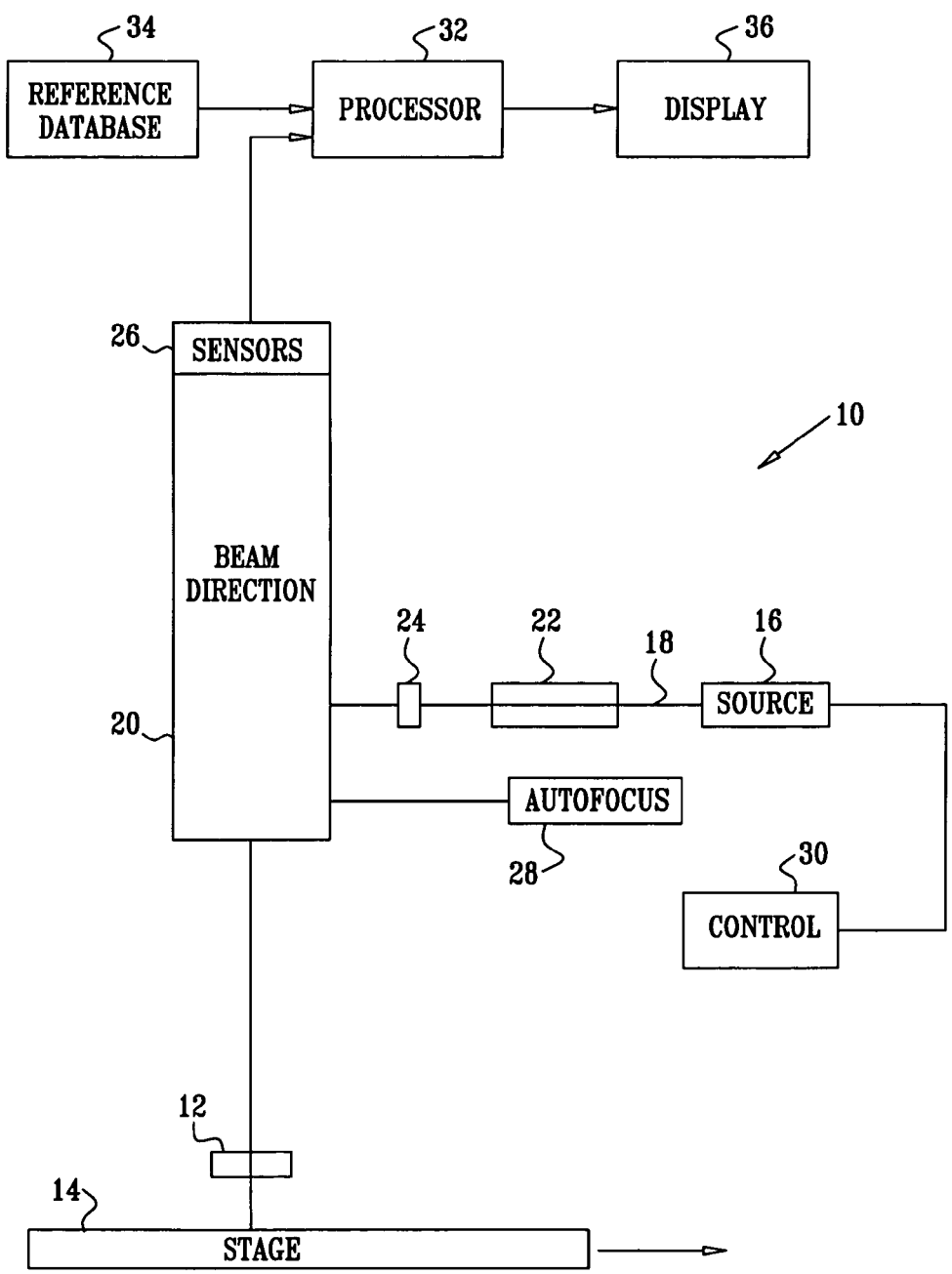
FIG. 1 is a schematic block diagram illustrating an opto-mechanical system for inspecting an article, which is constructed and operative in accordance with a disclosed embodiment of the invention.

Turning now to the drawings, reference is initially made to FIG. 1, which is a schematic block diagram illustrating an opto-mechanical system 10 for inspecting an article 12, which is constructed and operative in accordance with a disclosed embodiment of the invention. As explained below, the system 10 is shown as operating in a reflective mode for clarity of presentation. However, it is to be understood that inspection devices operating in a transmissive mode, or in both a transmissive and a reflective mode, are within the contemplation of the invention. The article 12, which is typically a wafer, a mask, or a reticle, is positioned on a x-y stage 14, which moves the article 12 in two directions within an inspection plane in a predetermined pattern of motion. The system 10 includes a light source 16, preferably a coherent light source, such as a laser, located on one side of the article 12. The light source 16 may be a continuous wave laser, or may be a pulsed laser, typically emitting short-wavelength laser beams in the UV or deep UV region. An illuminating beam 18 emitted by the light source 16 enters a beam directing subsystem 20, which includes transmission beam directing optics 22, and an optional coherence reduction optical apparatus 24. The beam directing subsystem 20 directs the beam 18 onto the surface of the article 12, and has specialized beam collection elements, which are disclosed in further detail hereinbelow. It should be noted that other means of directing the beam 18 onto the article 12, including other optical paths defined by suitable structure, also may be used.

The light beam hitting the surface of article 12 is reflected or transmitted as a collection beam via the beam directing subsystem 20 onto an imaging detector 26. The imaging detector 26 may be one or more CCD or CMOS sensors. The sensors could be a 1×M sensor, or a N×M area sensor or time delay integration (TDI) sensor. Alternatively, the imaging detector 26 may comprise multiple area sensors, as described hereinbelow. The imaging detector 26 is responsive to the detected changes in intensity and operative to develop signals corresponding thereto.

Oscillatory or stepped motion of the light beam hitting the surface of the article 12 may be used to scan the article 12. Alternatively the stage 14 carrying the article 12 can be moved continuously relative to the beam directing subsystem 20 in a predetermined pattern of motion. As a further alternative, the stage 14 may move the article in steps of appropriate size relative to the beam directing subsystem 20 between image capture positions. In any case, a relative displacement of the article 12 and the illuminating beam in a predetermined pattern of motion is produced. The system 10 may also include an autofocus device 28.

Although the system 10 as shown in FIG. 1 is configured for bright-field inspection of article 12, the principles of the present invention, as described hereinbelow, may similarly be used in dark-field inspection.

The light source 16 is controlled by a control system 30, which energizes the light source 16 to emit the beams in conjunction with the scanning of the stage 14. In some embodiments, the control system 30 is capable of varying the configuration and sensitivity of the imaging detector 26, and coordinating the operation of an image processor 32 as is described hereinbelow.

The output of the imaging detector 26 is linked to the image processor 32, optionally associated with a reference database 34. Results of the image processing are provided to the user on a display 36.

The collection beam contains information about the pattern on the article 12, and also provides information regarding any defects present in the article 12 and on its surface. Defects or contaminants in the optical components may cause unpredicted signal nonuniformities, thus making it harder to distinguish the defects, and may thus allow some microscopic defects to remain undetected. Therefore, there is a need to distinguish such system imperfections from true defects of the article 12.

Elements of the system 10 can be implemented using the apparatus disclosed in U.S. Pat. No. 6,587,194, or in U.S. Pat. No. 6,268,093, the disclosures of which are herein incorporated by reference.

Operation.

Figure 2:
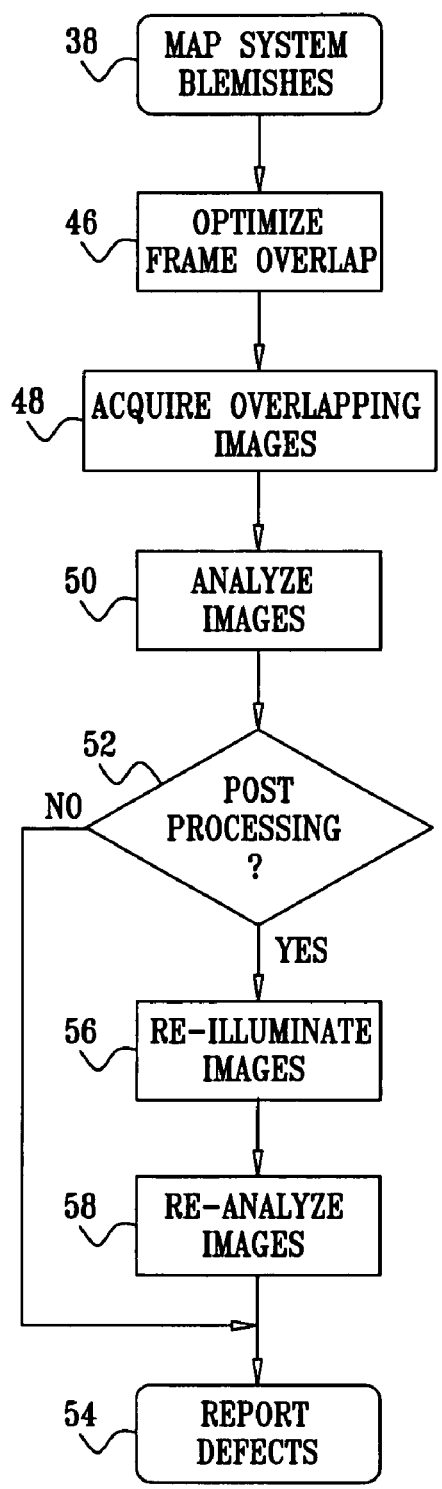
FIG. 2 is a flow diagram illustrating a multi-pass operation of the system shown in FIG. 1, in accordance with a disclosed embodiment of the invention.

With continued reference to FIG. 1, reference is now made to FIG. 2, which is a flow diagram illustrating a method of multi-pass inspection of an article in accordance with a disclosed embodiment of the invention. Each region on the mask is scanned at least twice and imaged in a detector, using an overlap, which is typically but not necessarily at least 50% between each two consecutive frames in the scan direction. Alternatively, more than one detector can be used. Advantages of other detection arrangements for producing images of the frames will become evident from the disclosure of other embodiments herein.

The method begins at initial step 38. This is a calibration stage in which pre-scan masking is accomplished. Pre-scan masking refers to the identification of system blemishes, so that they may be masked out of subsequent inspection images. Blank images are acquired as a composite calibration frame, which is then masked according to system blemishes that are present. As used herein, the term system blemishes generically includes contamination and other defects of the illumination system, the collection optics, as well as defects in the detector, such as defective pixels, and defects in any electronics required by the system. The calibration frame may be prepared using a blank article. It may be noted that system blemishes cannot be practically eliminated despite application of meticulous manufacturing and cleaning techniques to the inspection apparatus.

Figure 3:
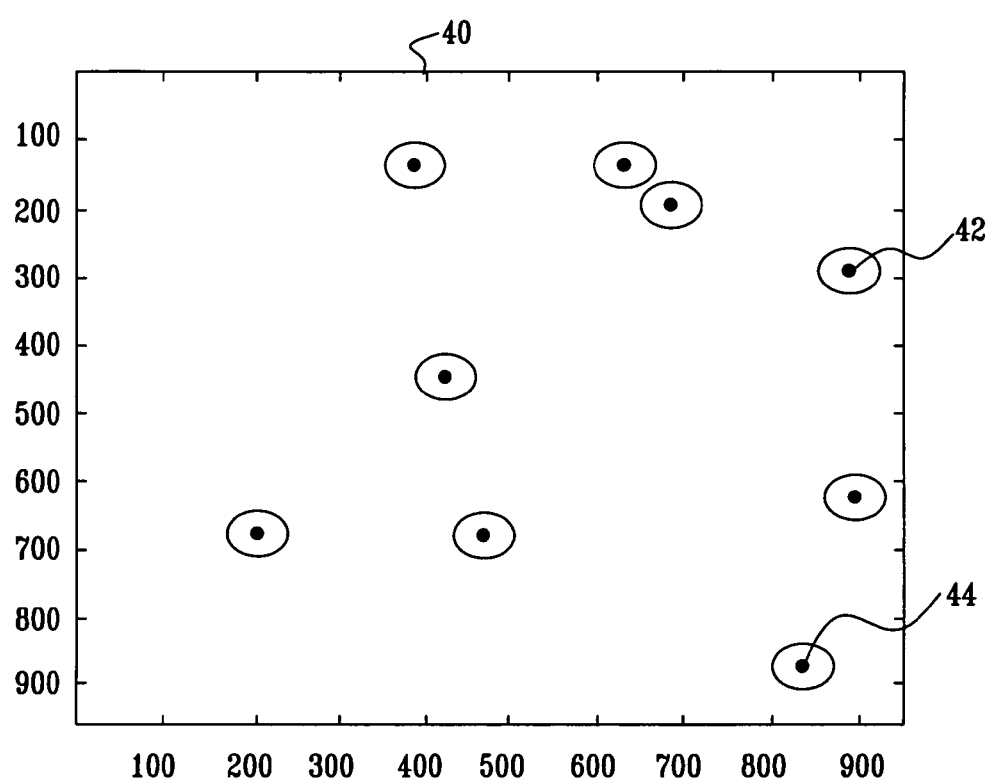
FIG. 3 is an image of a calibration frame prepared in accordance with a disclosed embodiment of the invention.

Reference is now made to FIG. 3, which is an image of a calibration frame 40 prepared in accordance with a disclosed embodiment of the invention as it would appear, for example on the display 36 (FIG. 1). Annuli 42, 44 are typical instances of optical artifacts that constitute one kind of system blemish.

Referring again to FIG. 2, after completion of initial step 38, control proceeds to step 46, where an optimal frame overlap is chosen. This is typically at least 50% of the frame area, but could be less than 50%. The latter would be possible, for example, if only a few blemishes were present and were generally not aligned along the scanning direction. System blemishes have substantially constant frame coordinates. That is, their coordinates are the same on all frame images. Mask defects have constant reticle coordinates, but inconstant frame coordinates. Indeed, all regions that are included on both of two successive frames have different coordinates on the two frames. The difference between the coordinates on the two frames is referred to herein as a "frame displacement". To assure that no region on a frame would be masked twice on two successive frames, all pairs of system blemishes that are aligned in the direction of the scan are identified, and the displacement between the members of the pairs determined. The frame overlap is selected such that the frame displacement does not coincide with any of the displacements associated with these pairs of blemishes. In the event that more than one frame overlap satisfies this condition, a minimum frame overlap is chosen. Step 46 is typically performed automatically. It may conveniently be performed offline, and thus can be accomplished by any processor, not necessarily the processor of the imaging system.

It should be noted that in some embodiments, described hereinbelow, more than two cameras may be used. In such cases, smaller frame overlaps are possible, as it is only necessary that no region on a frame be masked twice on any pair of cameras. In such embodiments, the output of one camera can be used to detect defects positioned at a blemish location of another. The advantages of such embodiments are increased throughput, at the expense of increased processing requirements.

Next, at step 48, images of overlapping regions of the article are acquired according to the frame overlap that was chosen at step 46.

Next, at step 50, the images acquired in step 48 are analyzed. Defects are identified. Each reported defect is labeled as masked (M) if its original pixel location, as acquired by the detector, corresponds to a system blemish, and unmasked (U) if it does not. Corresponding reticle coordinates in consecutive frames, wherein at least one apparent defect was identified, are identified and "clustered" together as pairs, so that each cluster or pair represents a single defect.

Four significant cases are distinguishable among the pairs:
M—a defect is reported once, in a masked region.
U—a defect is reported once, in a non-masked region.
UM—a defect is reported twice, once in a masked and once in an unmasked region.
UU—a defect is reported twice, both in a non-masked region.

A further case MM (twice masked) is not expected to occur, due to the calibration mentioned above. Instances of the case MM are automatically eliminated from further consideration.

Real defects are detected in different coordinates of consecutive frames, and the coordinates of these defects all have a known frame displacement on the two frames.

Optional post-processing procedures use different detection parameters for each case, due to different levels of suspicion that the various cases represent genuine defects.

By discarding the cases M and U, false positive detection caused by system instability, e.g., auto-focus problems, can be considerably reduced. Such problems rarely repeat themselves in the same manner in consecutive frames. Instances of the case UU are considered as genuine defects. Instances of the case UM are considered as probable defects. This case occurs when a true defect on the reticle coincides with a masked defect in one of two consecutive frames. However, as the unmasked member of the pair of the case UM has not been confirmed, there remains the possibility that it, too, is an instance of false positive detection, possibly due to system instability. Whether the case UM is characterized as a defect, or simply flagged for re-evaluation is controlled by a governing policy, which could be region-dependent. For example, in some areas of the reticle, defects could be inconsequential, in which case no further action would be necessary. In other regions, defects could be intolerable, and it would then be necessary to determine whether an instance of the case UM was a false positive detection, or a true defect. This could be accomplished, for example, by rescanning with a different frame registration on the article under inspection.

In some applications it is desirable to relax the detection thresholds of the imaging detector, in order to develop more instances of the cases UU and UM, and thereby improve the sensitivity of the inspection procedure. Decision step 52 is a determination whether such a policy is in effect.

If the determination at decision step 52 is negative, then control proceeds to final step 54. A report of the defects identified is generated for the user.

If the determination at decision step 52 is affirmative, then control proceeds to step 56. A redetection procedure is applied to defects that are detected twice, other than the case MM. In one mode of operation, the article is reilluminated by repeating step 48. This can be implemented using a detection algorithm, which combines information from the two sets of images. For instance, two corresponding images may be placed in registration and averaged in order to reduce noise. Alternatively, redetection can be implemented by reprocessing memorized data corresponding to the previously scanned images using different detection thresholds. This alternative is generally more efficient than reimaging the data. As a further alternative, redetection may be implemented by applying sub-pixel registration and averaging, or other known superresolution techniques. Alternatively, many combinations of the above mentioned techniques may be used to implement the redetection stage. It has been found that redetection can improve the signal-to-noise ratio by 40% as compared with the signal-to-noise ratio when only step 48 is performed.

Following completion of step 56, control proceeds to step 58, where the images are again analyzed. Step 58 is performed in the same manner as step 50. The details are not repeated in the interest of brevity. Control then proceeds to final step 54, which has been described above.

The principal downside of the above described technique is a reduction in system throughput by approximately a factor of two, as compared with a single pass inspection. In order to meet predetermined throughput requirements, it is possible to increase the pixel size. Such an increase might reduce the detection rate, but it could be balanced with the positive effect on the detection rate due to redetection.

In an alternative implementation of the above technique, frames are scanned such that there is an overlap between slices orthogonal to the scan direction. In this embodiment the frame displacement is measured orthogonal to the scan direction, and the frame overlap is chosen such that the frame displacement does not coincide with any of the displacements associated with pairs of blemishes that are aligned orthogonal to the scan direction. When system throughput is limited by stage speed, there is little advantage to this method. However, when processing time is the limiting factor, then this alternative may provide an advantage.

Throughput of the system 10 could be increased by using two or more cameras having a common field-of-view, with physical separation between the cameras provided by the use of beam splitters. Such a system would scan at a normal speed. This arrangement does not employ double inspection as described above. It would eliminate image sensor defects from consideration, but other forms of system contamination would continue to produce false positive detection, since their frame coordinates would be identical in both cameras.

Using a plurality of cameras in the system 10 together with the above-described double inspection technique could help to maintain reasonable inspection throughput, while solving the problems of defects both in the image sensor and the optical system. The main disadvantage of this method is that the beam splitters still reduce the light transmitted through to each camera. Providing enough fluence at the article plane to match the dynamic range of the camera is likely to exceed the damage threshold of surface layers on the article under inspection. Thus, this approach is impractical.

Embodiment 2

Figure 4:
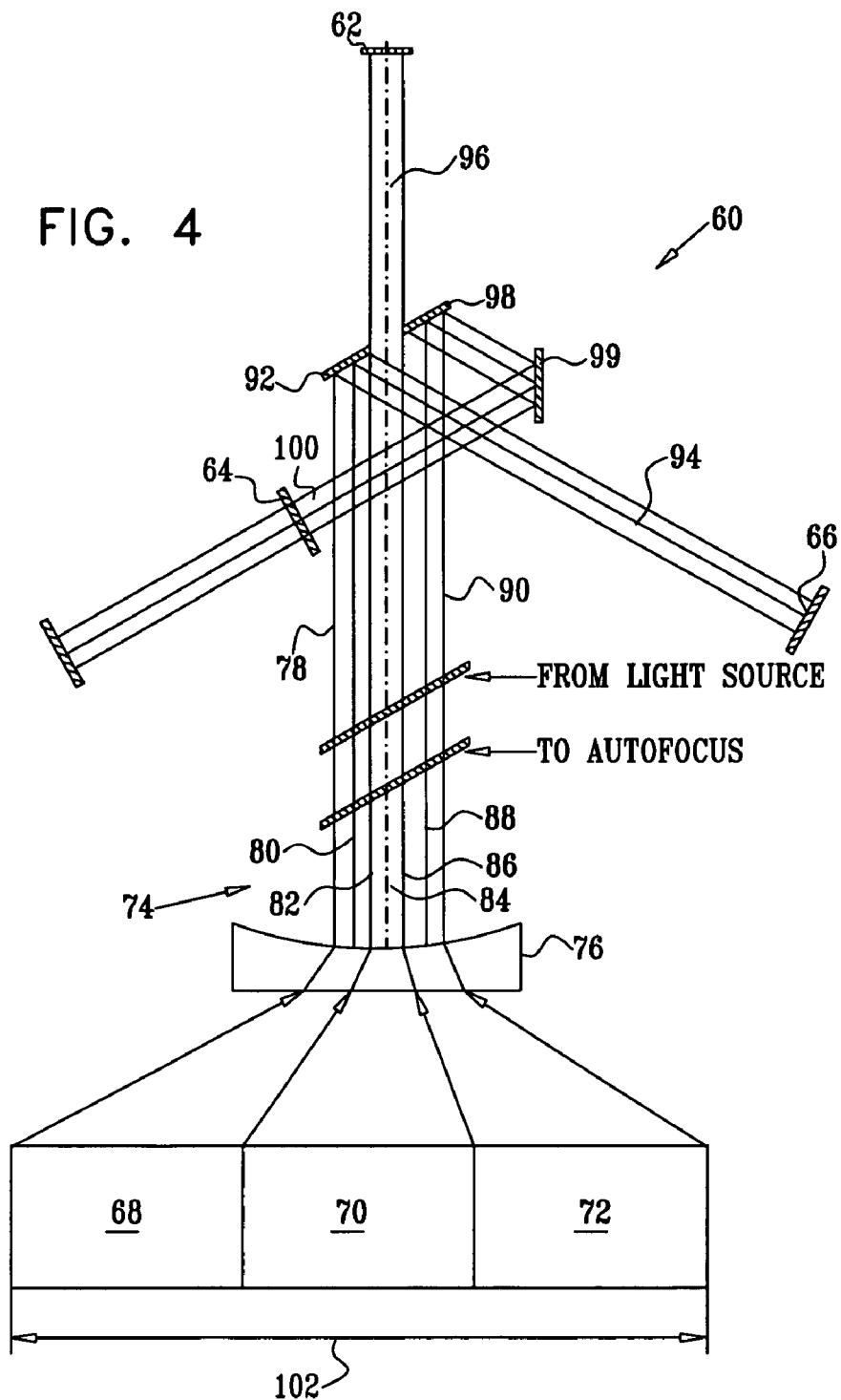
FIG. 4 is a schematic diagram of an optical system suitable for a scanning mode of operation, wherein each region on an article under inspection is viewed at least twice, which is constructed and operative in accordance with a disclosed embodiment of the invention.

Reference is now made to FIG. 4, which is a schematic diagram of beam directing optics 60, which are constructed and operative in accordance with a disclosed embodiment of the invention. The beam directing optics 60 can be implemented in the beam directing subsystem 20 of the system 10 (FIG. 1). Three cameras (not shown) are disposed at locations 62, 64, 66 for use as the imaging detector 26 (FIG. 1). In operation, as described above, respective fields of view 68, 70, 72 of the three cameras are non-overlapping, so that multiple images can be acquired simultaneously. The beam directing optics 60 are adapted to scan an article under inspection at a high throughput, using a high fluence, while preventing false positive detection resulting from contamination or other defects on the CCD and other optical surfaces of the system. Using inspection apparatus that incorporates the beam directing optics 60, it is possible to conduct inspection at high magnification without causing any damage to the inspected article.

A beam 74 is reflected or transmitted from an article and is collimated or focused by a suitable lens 76. The beam 74 has representative rays 78, 80, 82, 84, 86, 88, 90.

An optical element 92 reflects a part of the original beam 74 that is represented by the rays 78, 80 into a beam 94. Another part of the beam 74, which is represented by rays 82, 84, 86 is transmitted through the optical element 92 to form a beam 96. An Optical elements 98, 99 reflect a part of the original beam 74 that is represented by the rays 88, 90 into a beam 100.

In the beam directing optics 60, the locations 62, 64, 66 are established such that the paths of the beams 96, 94, 100 are equal in length. The transmission of light on each channel is kept as high as if only a single camera was used.

The optical elements 92, 98 may be constructed as a single unit, such that a central transparent area allows passage of the beam 96, and the beams 94, 100 are reflected by coated areas.

It can be seen that in the configuration of the beam directing optics 60, the overall instantaneous field of view 102 of the imaging system is increased, relative to any of the fields of view 68, 70, 72, each of which are a field of view of a single camera. The field of view 102 is typically rectangular, with the ratio between the sides equal to the number of cameras. Other mirror configurations are possible. Alternatively, the overall field of view may be square.

This arrangement provides a fast scan mode of operation, in which each of the three cameras (not shown) images its own field of view in the article plane without overlapping. In this fast scan mode, scanning takes place at a maximal speed $V = V_1 \cdot N$. Alternatively, the system can be optimized for multi-pass inspection at speed $V = V_1 \cdot N/2$, where V is the actual scanning speed, N is the number of cameras, and $V_1$ is the scanning speed that would be required for a single camera to scan the article 12 (FIG. 1) in a single pass with the same resolution.

While provision in FIG. 4 is made for three cameras, this is merely exemplary. The beam directing optics 60 may be modified by those skilled in the art to provide locations for a larger number of cameras, or for only two cameras. Embodiments using more than three cameras may be configured for simultaneous scanning using different overlaps in the fields of view. In such embodiments an instance of the case UM could resolve into a case UUM or a case U-M, (where the symbol "-" represents absence of a defect indication). Embodiments using three or fewer cameras can also be configured to scan with different frame overlaps, but at the cost of decreased throughput. The information provided by such embodiments could thus be used to increase the accuracy of classification of these instances.

Embodiment 3

Figure 5:
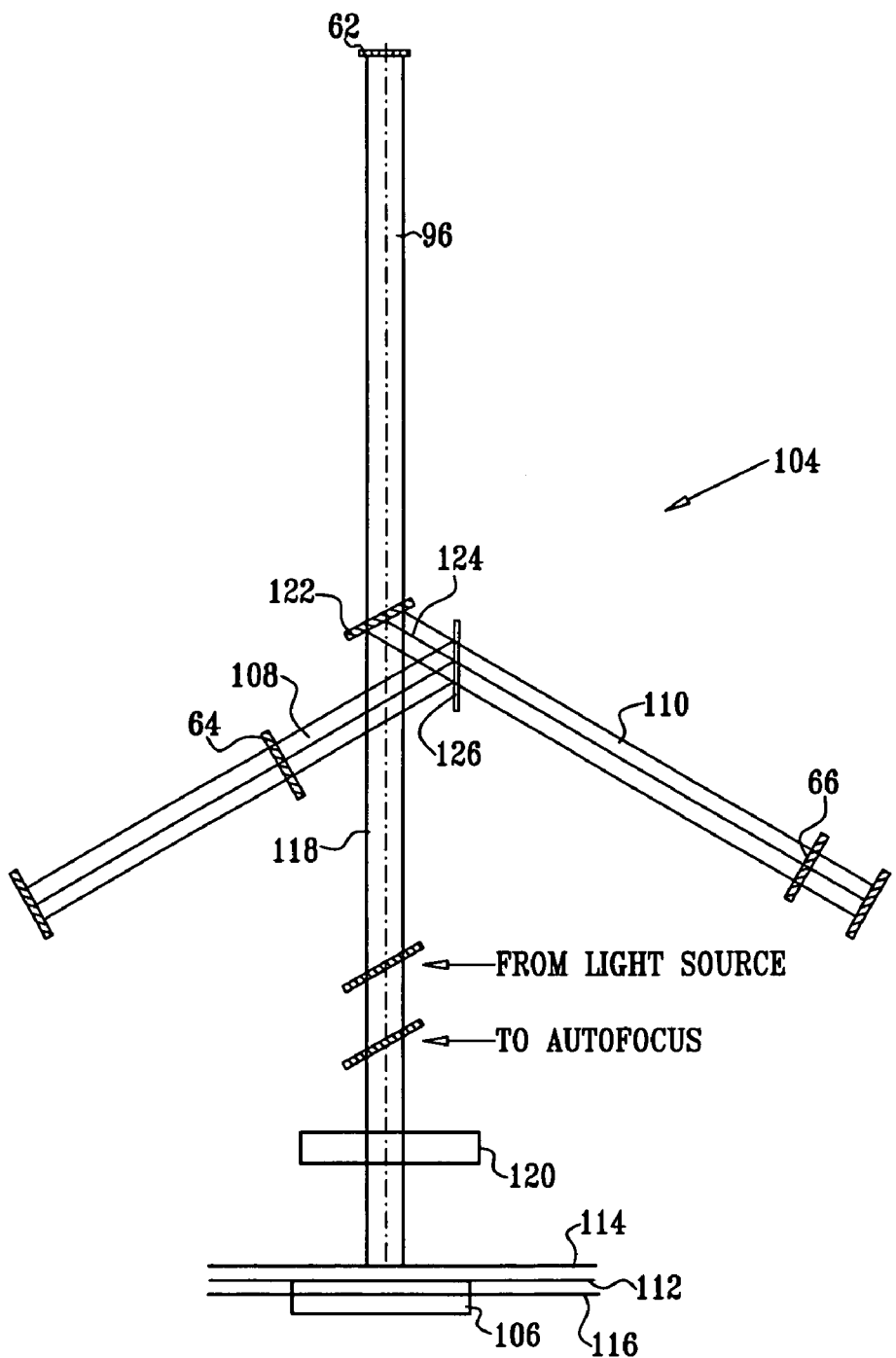
FIG. 5 is a schematic diagram of an optical system for performing multi-focal optical inspection suitable for evaluation of a process window, which is constructed and operative in accordance with a disclosed embodiment of the invention.

Reference is now made to FIG. 5, which is a schematic diagram of beam directing optics 104, which are constructed and operative in accordance with a disclosed embodiment of the invention. The beam directing optics 104 may be implemented in the beam directing subsystem 20 (FIG. 1), and are useful for applications in which a focal range, or process window, is to be evaluated on an article 106 under inspection. The beam directing optics 104 can be used, for example, in the inspection of phase shift masks.

The beam directing optics 104 include three cameras (not shown) at the locations 62, 64, 66, which are adjusted to have the same field of view during a given time frame. While provision in FIG. 5 is mode for three cameras, this is merely exemplary. Applying the principles of the invention, the beam directing optics 104 may be modified by those skilled in the art to provide locations for a larger or smaller number of cameras, which can modify the resolution at which the process window is evaluated.

In the beam directing optics 104, the locations 62, 64, 66 are established such that the effective optical paths of the beams 96, 94, 100 are different in length. This may be accomplished by moving the locations 62, 64, 66 along the optical axes of their respective beams 96, 108, 110 such that optical paths extending from the article 106 to the location 64, from the article 106 to the location 62, and from the article 106 to the location 66 all differ in length. Thus, cameras (not shown) disposed at the locations 62, 64, 66 all have the same field of view on the article under inspection, but are placed in different defocus. Typically, one camera is focused on the surface of the article 106, indicated as a focal plane 112. Another camera is defocused slightly on a focal plane 114 above the surface of the article. The third camera is defocused slightly on a focal plane 116 below the surface of the article 106.

A beam 118 is reflected or transmitted from the article 106 via a suitable objective lens 120, and strikes a 2:1 beam splitter 122. One third of the beam 118 continues toward the location 62 as the beam 96. Two thirds of the beam 118 form a beam 124. The beam 124 is directed to a beam splitter 126, and divides equally into the beam 108 and the beam 110, which are directed to locations 64, 66, respectively.

As a result of the optical arrangement of the beam directing optics 104 the beams 96, 108, 110 arrive with equal fluence at the locations 62, 64, 66, respectively.

Embodiment 4

The beam directing optics 104 may be realized as a modification of the beam directing optics 60 (FIG. 4) in which the beam splitters 122, 126 have been added, and the rays 78, 80, 88, 90 are blocked, for example with a shutter, so that the mirrors 92, 98 become nonfunctional. Alternatively, the mirrors 92, 98 may be moved out of the path of the beam 74.

Figure 6:
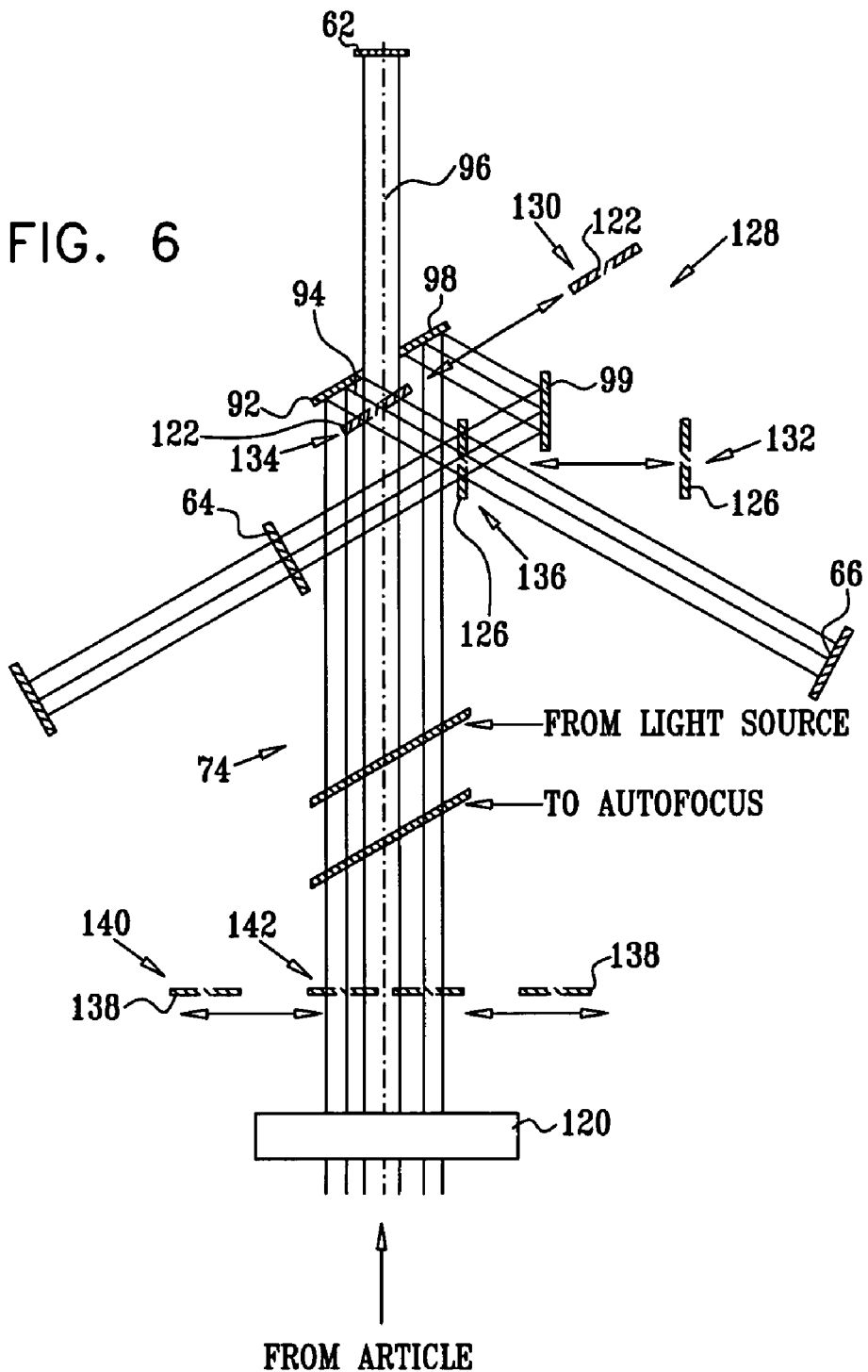
FIG. 6 is a composite schematic diagram of an opto-mechanical system in which configurations of the embodiments shown in FIG. 4 and FIG. 5 are interchangeable, which is constructed and operative in accordance with a disclosed embodiment of the invention.

Reference is now made to FIG. 6, which is a composite schematic diagram of beam directing optics 128, which is constructed and operative in accordance with a disclosed embodiment of the invention. The system 128 can be implemented in the beam directing subsystem 20 (FIG. 1). In the beam directing optics 128, the configurations of the beam directing optics 60 (FIG. 4) and the beam directing optics 104 (FIG. 5) can be interchanged. When it is desired to change from the configuration of the beam directing optics 60 (FIG. 4) to that of the beam directing optics 104. (FIG. 5), the beam splitters 122, 126 are simply moved from non-operating positions 130, 132 into operating positions 134, 136, respectively, and a portion of the beam 74 is blocked by moving a shutter 138 from an open position 140 to a closed position 142, so that the mirrors 92, 98 are not operative to reflect any portion of the beam 74. The cameras (not shown) are all set to focus on different planes, as described above in the discussion of FIG. 4. These operations are reversed when it is desired to reassume the configuration of the beam directing optics 60 (FIG. 4), in which case the cameras (not shown) are set to focus on the plane of the surface of the article under inspection.

Scanning.

Figure 7:
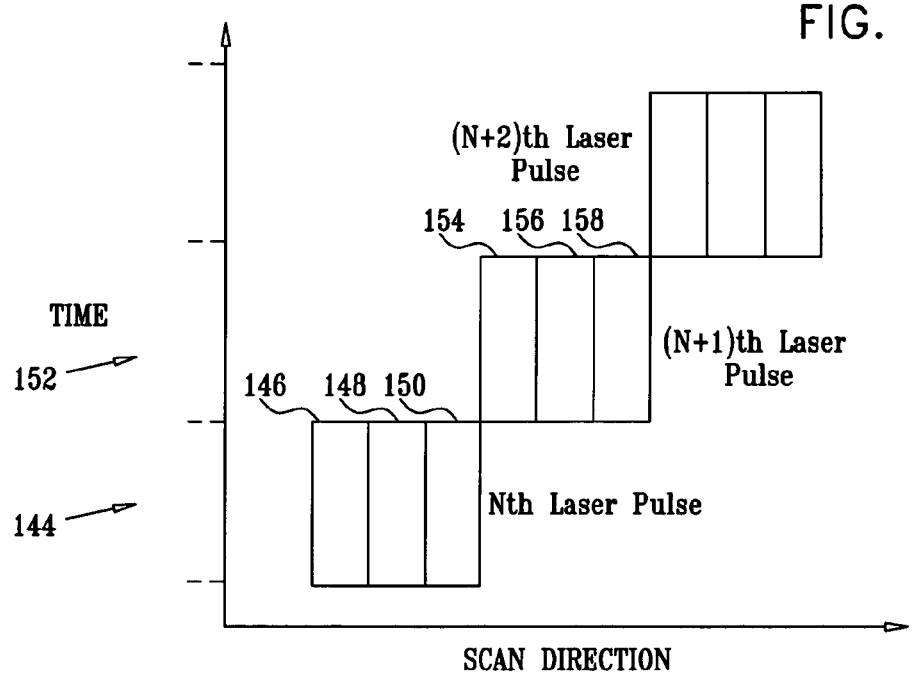
FIG. 7 schematically illustrates a fast scanning mode of operation using three cameras, in accordance with a disclosed embodiment of the invention.

With continued reference to FIG. 4, FIG. 5, and FIG. 6, the scanning scheme used in the beam directing optics 104 or the beam directing optics 60 depends on the operational mode. A fast mode of operation, using pulsed laser light, may be used when the effect of contamination defects is negligible. Fast mode scanning requires moving the article stage between the laser pulses by a distance corresponding to one camera field of view multiplied by a number of cameras. Reference is now made to FIG. 7, which schematically illustrates a fast scanning mode of operation using three cameras, in accordance with a disclosed embodiment of the invention. During a first time interval 144, demarcated by dashed lines along the vertical axis, a $N^{th}$ laser pulse occurs. The cameras (not shown) have respective fields of view 146, 148, 150. In a second time interval 152, the scan has progressed along the scanning direction, shown as the horizontal axis in FIG. 7. During the time interval 152, a $N+1^{th}$ laser pulse occurs, The cameras now have fields of view 154, 156, 158, which are displaced to the right with respect to the fields of view 146, 148, 150. The fields of view 146, 148, 150, 154, 156, 158 are non-overlapping.

The scanning scheme for multi-pass inspection to improve the system detection capability is different. It will be recalled that each inspected area must be imaged at least twice. This is accomplished by providing area overlap in the fields of view of different cameras.

Figure 8:
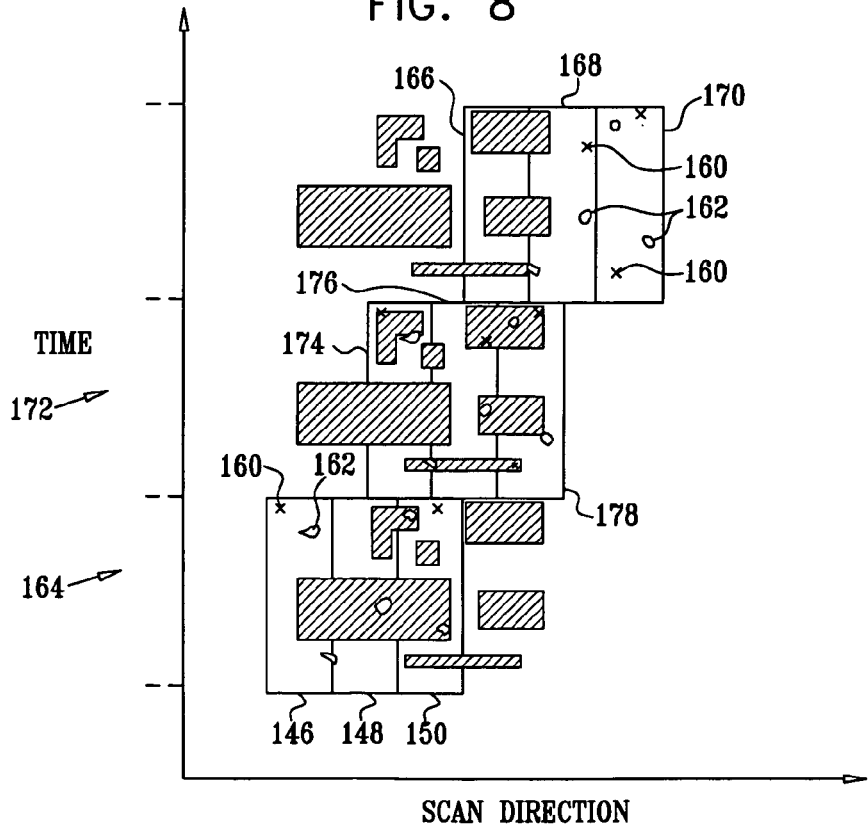
FIG. 8 schematically illustrates multi-pass scanning in accordance with a disclosed embodiment of the invention.

Reference is now made to FIG. 8, which schematically illustrates multi-pass scanning in accordance with a disclosed embodiment of the invention. As in the mode disclosed with respect to FIG. 7, pulsed laser light is used. The article pattern, indicated by hatched areas, is replicated in each time interval in order to illustrate discrete changes in the camera fields of view with respect to time. Defective pixels 160 and contaminated areas 162 are shown. In a first time interval 164, a $N^{th}$ laser pulse occurs, and three cameras (not shown) have fields of view 166, 168, 170. In a second time interval 172, a $N+1^{th}$ laser pulse occurs, and the three cameras have fields of view 174, 176, 178. It will be noted that the field of view 148 overlaps the field of view 174. Similarly, the field of view 150 overlaps the field of view 176. As explained above, the overlaps should be at least 50%. In this manner, there is always at least one frame in which every point in the pattern can be observed without coinciding with a system blemish.

Referring again to FIG. 4, multi-pass scanning according to the invention has the advantages that a beam originating from a total field of view during a time interval passes through different optical paths and is imaged on different cameras. The fluence with regard to each camera is essentially equated by maximizing the use of mirrors instead of beam splitters. As a result, the fluence at the article plane is minimized, and a high signal-to-noise ratio is achieved. The inventive scheme permits switching to multi-focus inspection by minor focusing adjustments in the cameras. The optical arrangements of FIG. 5 and FIG. 4 can be realized using commercially available optical elements.

It will be appreciated by persons skilled in the art that the present invention is not limited to what has been particularly shown and described hereinabove. Rather, the scope of the present invention includes both combinations and sub-combinations of the various features described hereinabove, as well as variations and modifications thereof that are not in the prior art, which would occur to persons skilled in the art upon reading the foregoing description.

The invention claimed is:

1. A method comprising the steps of:
   acquiring a first frame image of a first field of view of an article;
   acquiring a second frame image of a second field of view of said article, wherein said first field of view and said second field of view have an overlap;
   inspecting said first frame image and said second frame image;
   identifying system blemishes, said blemishes having substantially identical locations on said first frame image and said second frame image; and
   masking said system blemishes.

2. The method according to claim 1, further comprising the step of identifying a first defect location on said first frame image and a second defect location on said second frame image, said first defect location being displaced from said second defect location by a frame displacement that is defined by said overlap, wherein at least one of said first defect location and said second defect location is distinct from any of said blemish locations.

3. The method according to claim 2, wherein both of said first defect location and said second defect location are distinct from said blemish locations.

4. The method according to claim 2, further comprising the step of adjusting said overlap such that said frame displacement is distinct from displacements between members of pairs of system blemishes that are aligned in a scan direction.

5. The method according to claim 2, further comprising the steps of:
   varying a detection threshold of said first frame image and said second frame image; and
   repeating said step of identifying said first defect location on said first frame image and said second defect location on said second frame image, so as to identify all defect locations on said article.

6. The method according to claim 2, further comprising the steps of:
   applying a super-resolution technique to said first frame image and said second frame image; and
   repeating said step of identifying said first defect location on said first frame image and said second defect location on said second frame image, so as to identify all defect locations on said article.

7. The method according to claim 1, wherein said steps of acquiring said first frame image and acquiring said second frame image are performed by impinging pulsed coherent light on said article.

8. The method according to claim 1, wherein a focal plane of said first frame image differs from a focal plane of said second frame image.

9. The method according to claim 1, wherein said overlap of said first field of view and said second field of view is oriented in a scan direction.

10. The method according to claim 1, wherein said overlap of said first field of view and said second field of view is oriented orthogonal to a scan direction.

11. The method according to claim 1, wherein said overlap is at least 50% of an area of said first frame image.

12. A method comprising the steps of:
disposing a plurality of image sensors to image an article;
acquiring images of the article, by directing a collection beam from a surface of said article under inspection onto said image sensors, in a first configuration in which all said image sensors have a common field of view, and in a second configuration in which said image sensors have different fields of view comprising a first field of view and a second field of view; and
inspecting the images.

13. The method according to claim 12, wherein said collection beam is directed onto said image sensors with equal fluence.

14. The method according to claim 12, wherein three said image sensors are disposed, and said collection beam is directed toward said image sensors by two mirrors.

15. The method according to claim 12, wherein in said first configuration said image sensors are focused on different planes relative to said surface of said article.

16. The method according to claim 12, wherein in said second configuration said first field of view has an overlap with said second field of view.

17. The method according to claim 16, wherein said overlap exceeds 50 per cent, wherein a frame displacement between said first field of view and said second field of view is distinct from displacements between members of pairs of system blemishes that are aligned in a scan direction.

18. The method according to claim 12, further comprising the step of disposing at least one beam splitter in said collection beam for directing at least portions of said collection beam toward said image sensors, respectively.

19. The method according to claim 18, wherein said beam splitter comprises two beam splitters, and said image sensors comprise three image sensors.

20. The method according to claim 18, further comprising the steps of:
disposing a mirror in said collection beam, and disposing a beam blocking means so as to block a portion of said collection beam from reaching said mirror;
displacing said beam blocking means and said beam splitter between operating positions and non-operating positions;
scanning said article relative to said image sensors in a scan direction; wherein:
in said first configuration said beam blocking means is interposed so as to block said portion of said collection beam, and said beam splitter is disposed within said collection beam;
in said second configuration said beam blocking means and said beam splitter are displaced external to said collection beam, and
said first field of view and said second field of view have an overlap, and a frame displacement between said first field of view and said second field of view is distinct from displacements between members of pairs of system blemishes that are aligned in said scan direction.

21. The method according to claim 20, wherein said overlap exceeds 50 per cent in said scan direction, wherein said frame displacement is distinct from displacements between said members of pairs of system blemishes that are aligned in said scan direction.

22. The method according to claim 20, wherein said overlap exceeds 50 per cent in an orthogonal direction to said scan direction, wherein said frame displacement in said orthogonal direction is distinct from displacements between said members of pairs of system blemishes that are aligned in said orthogonal direction.

23. The method according to claim 20, wherein in said first configuration said image sensors are focused on different planes relative to said surface of said article.

* * * * *